(12) United States Patent
Govari

(10) Patent No.: US 6,373,240 B1
(45) Date of Patent: Apr. 16, 2002

(54) METAL IMMUNE SYSTEM FOR TRACKING SPATIAL COORDINATES OF AN OBJECT IN THE PRESENCE OF A PERTURBED ENERGY FIELD

(75) Inventor: Assaf Govari, Haifa (IL)

(73) Assignee: Biosense, Inc., New Burnswick, NJ (US)

( * ) Notice: Subject to any disclaimer, the term of this patent is extended or adjusted under 35 U.S.C. 154(b) by 0 days.

(21) Appl. No.: 09/702,973

(22) Filed: Oct. 31, 2000

Related U.S. Application Data

(63) Continuation-in-part of application No. 09/173,763, filed on Oct. 15, 1998, now Pat. No. 6,147,480.

(51) Int. Cl.[7] ............................................... G01B 7/14
(52) U.S. Cl. .................. 324/207.17; 702/150; 702/152
(58) Field of Search ........................... 324/207–17, 260, 324/461, 67; 342/442, 448, 459; 336/5; 607/422, 122; 702/150, 152, 153

(56) References Cited

U.S. PATENT DOCUMENTS

| | | |
|---|---|---|
| 3,644,825 A | 2/1972 | Davis, Jr. et al. |
| 3,868,565 A | 2/1975 | Kuipers |
| 4,017,858 A | 4/1977 | Kuipers |
| 4,054,881 A | 10/1977 | Raab |
| 4,317,078 A | 2/1982 | Weed et al. |
| 4,416,289 A | 11/1983 | Bresler |
| 4,526,177 A | 7/1985 | Rudy et al. |
| 4,560,930 A | 12/1985 | Kouno |
| 4,613,866 A | 9/1986 | Blood |
| 4,642,786 A | 2/1987 | Hansen |

(List continued on next page.)

FOREIGN PATENT DOCUMENTS

| | | |
|---|---|---|
| WO | WO92/03090 A1 | 3/1992 |
| WO | WO94/04938 A1 | 3/1994 |
| WO | WO94/23647 A1 | 10/1994 |
| WO | WO96/05768 A1 | 2/1996 |
| WO | WO96/41119 A1 | 12/1996 |
| WO | WO97/29678 A1 | 8/1997 |
| WO | WO97/29679 A1 | 8/1997 |
| WO | WO97/29709 A1 | 8/1997 |
| WO | WO97/29710 A1 | 8/1997 |
| WO | WO97/32179 A1 | 9/1997 |
| WO | WO97/42517 A1 | 11/1997 |

*Primary Examiner*—Edward Lefkowitz
*Assistant Examiner*—Subhash Zaveri
(74) *Attorney, Agent, or Firm*—Louis J. Capezzuto

(57) ABSTRACT

A method for tracking an object, including producing an unperturbed energy field at a plurality of predetermined frequencies in the vicinity of the object and determining a characteristic of a perturbing energy field induced responsive to the unperturbed field, due to introduction of an article, responsive to the unperturbed field, into the vicinity of the object. The method further includes receiving a plurality of resultant signals responsive to the unperturbed and perturbing energy fields generated at a location of the object after introduction of the article, determining an optimal frequency for the unperturbed energy field from amongst the plurality of predetermined frequencies responsive to a parameter of the resultant signals, and determining spatial coordinates of the object responsive to the resultant signal at the optimal frequency.

19 Claims, 3 Drawing Sheets

U.S. PATENT DOCUMENTS

| | | |
|---|---|---|
| 4,651,436 A | 3/1987 | Gaal |
| 4,710,708 A | 12/1987 | Rorden et al. |
| 4,849,692 A | 7/1989 | Blood |
| 4,905,698 A | 3/1990 | Strohl, Jr. et al. |
| 4,945,305 A | 7/1990 | Blood |
| 5,002,137 A | 3/1991 | Dickinson et al. |
| 5,042,486 A | 8/1991 | Pfeiler et al. |
| 5,068,608 A | 11/1991 | Clark, Jr. |
| 5,099,845 A | 3/1992 | Besz et al. |
| 5,172,056 A | 12/1992 | Voisin |
| 5,211,165 A | 5/1993 | Dumoulin et al. |
| 5,251,635 A | 10/1993 | Dumoulin et al. |
| 5,253,647 A | 10/1993 | Takahashi et al. |
| 5,255,680 A | 10/1993 | Darrow et al. |
| 5,265,610 A | 11/1993 | Darrow et al. |
| 5,269,289 A | 12/1993 | Takehana et al. |
| 5,273,025 A | 12/1993 | Sakiyama et al. |
| 5,309,913 A | 5/1994 | Kormos et al. |
| 5,325,873 A | 7/1994 | Hirschi et al. |
| 5,375,906 A | 12/1994 | Twiss et al. |
| 5,377,678 A | 1/1995 | Dumoulin et al. |
| 5,425,367 A | 6/1995 | Shapiro et al. |
| 5,425,382 A | 6/1995 | Golden et al. |
| 5,429,132 A | 7/1995 | Guy et al. |
| 5,437,277 A | 8/1995 | Dumoulin et al. |
| 5,443,489 A | 8/1995 | Ben-Haim |
| 5,453,687 A | 9/1995 | Zierdt et al. |
| 5,558,091 A | 9/1996 | Acker et al. |
| 5,577,502 A | 11/1996 | Darrow et al. |
| 5,622,169 A | 4/1997 | Golden et al. |
| 5,682,886 A | 11/1997 | Delp et al. |
| 5,694,945 A | 12/1997 | Ben-Haim |
| 5,715,822 A | 2/1998 | Watkins et al. |
| 5,729,129 A | 3/1998 | Acker |
| 5,752,513 A | 5/1998 | Acker et al. |
| 5,769,843 A | 6/1998 | Abela et al. |
| 6,147,480 A * | 11/2000 | Osadchy et al. ............... 324/67 |
| 6,226,547 B1 * | 5/2001 | Lockhrt et al. ............. 600/424 |

\* cited by examiner

METAL IMMUNE SYSTEM FOR TRACKING SPATIAL COORDINATES OF AN OBJECT IN THE PRESENCE OF A PERTURBED ENERGY FIELD

CROSS-REFERENCE TO RELATED APPLICATIONS

This application is a continuation-in-part of U.S. patent application No. 09/173,763 filed Oct. 15, 1998 now U.S. Pat. No. 6,147,480 which is incorporated herein by reference.

FIELD OF THE INVENTION

The present invention relates generally to non-contact tracking of objects using a magnetic field, and specifically to counteracting the effect of an intruding field-responsive article in the field.

BACKGROUND OF THE INVENTION

Non-contact electromagnetic tracking systems are well known in the art, with a wide range of applications.

U.S. Pat. No. 5,391,199, to Ben-Haim, which is assigned to the assignee of the present application and whose disclosure is incorporated herein by reference, describes a system for generating three-dimensional location information regarding a medical probe or catheter. A sensor coil is placed in the catheter and generates signals in response to externally applied magnetic fields. The magnetic fields are generated by three radiator coils, fixed to an external reference frame in known, mutually spaced locations. The amplitudes of the signals generated in response to each of the radiator coil fields are detected and used to compute the location of the sensor coil. Each radiator coil is preferably driven by driver circuitry to generate a field at a known frequency, distinct from that of other radiator coils, so that the signals generated by the sensor coil may be separated by frequency into components corresponding to the different radiator coils.

PCT patent publication WO/96/05768, filed Jan. 24, 1995, which is assigned to the assignee of the present application and whose disclosure is incorporated herein by reference, describes a system that generates six-dimensional position and orientation information regarding the tip of a catheter. This system uses a plurality of sensor coils adjacent to a locatable site in the catheter, for example near its distal end, and a plurality of radiator coils fixed in an external reference frame. These coils generate signals in response to magnetic fields generated by the radiator coils, which signals allow for the computation of six location and orientation coordinates. As in the case of the '539 patent application described above, the radiator coils preferably operate simultaneously at different frequencies, for example at 1000, 2000 and 3000 Hz, respectively.

The above tracking systems rely on separation of position-responsive signals into components, most typically frequency components, wherein each such component is assumed to correspond uniquely to a single radiator coil, in a known position, radiating a magnetic field having a regular, well-defined spatial distribution. In practice, however, when a metal or other magnetically-responsive article is brought into the vicinity of the catheter or other object being tracked, the magnetic fields generated in this vicinity by the radiator coils are distorted. For example, the radiator coil's magnetic field may generate eddy currents in such an article, and the eddy currents will then cause a parasitic magnetic field to be radiated. Such parasitic fields and other types of distortion can lead to errors in determining the position of the object being tracked.

U.S. Pat. No. 5,767,669 to Hansen et al., whose disclosure is incorporated herein by reference, describes a method for subtracting eddy current distortions produced in a magnetic tracking system. The system utilizes pulsed magnetic fields from a plurality of generators, and the presence of eddy currents is detected by measuring rates of change of currents generated in sensor coils used for tracking. The eddy currents are compensated for by adjusting the duration of the magnetic pulses.

U.S. Pat. No. 4,945,305 to Blood, whose disclosure is incorporated herein by reference, describes a tracking system which avoids the problems of eddy currents by using pulsed DC magnetic fields. Sensors which are able to detect DC fields are used in the system, and eddy currents are detected and adjusted for by utilizing the decay characteristics and the amplitudes of the eddy currents.

European Patent Application EP 0964261A2, to Dumoulin, whose disclosure is incorporated herein by reference, describes systems for compensating for eddy currents in a tracking system using alternating magnetic field generators. In a first system the eddy currents are compensated for by first calibrating the system free from eddy currents, and then modifying the fields generated when the eddy currents are detected. In a second system the eddy currents are nullified by using one or more shielding coils placed near the generators.

FIG. 1 is a graph showing a relation of the permeability $\mu$ of a ferromagnetic material in a magnetic field vs. frequency f at which the field is being generated, as is known in the art. Permeability $\mu$ is a factor in the phase shift generated by the magnetic field. The graph applies to a change of the permeability $\mu$ of the ferromagnetic material, generated for an article wherein eddy currents are formed. The change reflects the phase shift in a sensor, caused by the article, vs. the frequency f As. is known in the art, additional factors affecting the phase shift are geometry of the article, and conductivity of the material. The graph shows a virtually linear change in permeability for small changes in frequency.

SUMMARY OF THE INVENTION

It is an object of some aspects of the present invention to provide methods and apparatus for non-contact tracking of an object in an energy field in the presence of an article which interferes with the field.

It is another object of some aspects of the present invention to provide methods and apparatus for minimizing the effect of an article which interferes with an energy field used for non-contact tracking of an object.

In a preferred embodiment of the present invention, an object tracking system comprises one or more sensor coils adjacent to a locatable point on an object being tracked, and one or more radiator coils, which generate alternating energy fields comprising magnetic fields, in a vicinity of the object when driven by respective alternating electrical currents. For each radiator coil, a frequency of its alternating electrical current is scanned through a plurality of values so that, at any specific time, each of the radiator coils radiates at a frequency which is different from the frequencies with which the other radiator coils are radiating.

The sensor coils generate electrical signals responsive to the magnetic fields, which signals are received by signal processing circuitry and analyzed by a computer or other processor. When a metal or other field-responsive article is in the vicinity of the object, the signals typically include position signal components responsive to the magnetic fields generated by the radiator coils at their respective instantaneous driving frequencies, and parasitic signal components responsive to parasitic magnetic fields generated due to the article. The parasitic components are typically equal in frequency to the instantaneous frequency of the driving frequency, but are shifted in phase, so that the effect at each sensor coil is to produce a combined signal having a phase and an amplitude which are shifted relative to the signal when no field-responsive article is present. The phase-shift is a function of the driving frequency, and so will vary as each driving frequency is scanned. The computer processes the combined signal to find which frequency produces a minimum phase-shift, and thus a minimum effect of the parasitic components, and this frequency is used to calculate the position of the object. Varying the driving frequency until the phase shift is a minimum is an effective method, not known in the art, for reducing the effect of field-responsive articles on the signal.

In preferred embodiments of the present invention, an alternative method is also used in order to find a value of the position signal, i.e., of the signal produced without interfering effects of the field-responsive article. Measurements of the value of the combined signal are made at a plurality of frequencies. The values obtained are used to solve a plurality of simultaneous equations comprising the position signal as one of the unknowns in the equations. Thus, varying the driving frequency enables the position signal to be determined in the presence of interfering signals from field-responsive articles.

The present invention relies on the fact that parasitic magnetic fields, generated by metal or other field-responsive articles that receive and re-radiate energy from a radiator coil magnetic field are typically at the same frequency as the radiator coil field, but are shifted in phase relative thereto. The phase shift and the amplitudes of the parasitic fields generally depend on properties of the article, including dielectric constant, magnetic permeability and geometrical shape.

However, both the phase shift and the amplitude of the parasitic fields can be assumed to be linearly dependent on the value of the frequency generating the parasitic field.

There is therefore provided, according to a preferred embodiment of the present invention, a method for tracking an object including:

producing an unperturbed energy field at a plurality of predetermined frequencies in the vicinity of the object;

determining a characteristic of a perturbing energy field induced responsive to the unperturbed field, due to introduction of an article responsive to the unperturbed field into the vicinity of the object;

receiving a plurality of resultant signals responsive to the unperturbed and perturbing energy fields generated at a location of the object after introduction of the article;

determining an optimal frequency for the unperturbed energy field from amongst the plurality of predetermined frequencies responsive to a parameter of the resultant signals; and determining spatial coordinates of the object responsive to the resultant signal at the optimal frequency.

Preferably, producing the unperturbed energy field at the plurality of predetermined frequencies includes scanning the frequencies sequentially.

Further preferably, producing the unperturbed energy field at the plurality of predetermined frequencies includes multiplexing at least some of the frequencies.

Preferably, receiving the plurality of resultant signals includes:

measuring a baseline phase value $\phi_{107}$ of each of the plurality of resultant signals at the respective plurality of predetermined frequencies before introduction of the article; and measuring a phase shift $\phi_\omega^{total}$ at the respective plurality of predetermined frequencies after introduction of the article, so that the parameter comprises a term $|\phi_\omega^{total} - \phi_\omega|$ for each of the plurality of predetermined frequencies; and wherein determining the optimal frequency includes determining a frequency $\omega$ at which $|\phi_\omega^{total} - \phi_\omega|$ is a minimum.

Preferably, determining spatial coordinates of the object includes determining spatial coordinates responsive to an amplitude of a signal $|M\omega|$ at the frequency $\omega$.

Further preferably, determining spatial coordinates of the object includes determining spatial coordinates responsive to a phase of a signal $M_\omega$ at the frequency $\omega$.

Preferably, producing the energy fields includes producing magnetic fields. Preferably, receiving the signals includes receiving electrical signals which are generated responsive to the magnetic fields.

There is further provided, according to a preferred embodiment of the present invention, a method for tracking an object, including:

producing an unperturbed energy field comprising a plurality of predetermined frequencies in the vicinity of the object;

producing a perturbing energy field by introduction of an article responsive to the unperturbed field into the vicinity of the object;

receiving a respective plurality of signals responsive to the unperturbed and perturbing energy fields generated at a location of the object after introduction of the article; and determining one or more factors conditional on spatial coordinates of the object responsive to the plurality of signals and the respective frequencies.

Preferably, determining the one or more factors includes:

assuming a phasor $\overline{A}_\omega$ of a signal responsive to the unperturbed energy field and a phasor $\overline{A}'_\omega$ of a signal responsive to the perturbing energy field to be directly proportional to a plurality of predetermined currents generating the fields; and assuming a phase $\phi_\omega$ of the signal responsive to the unperturbed energy field and a phase $\phi_\omega'$ of the signal responsive to the perturbing energy field to be linearly dependent on the plurality of predetermined frequencies.

Preferably, the plurality of frequencies includes at least four frequencies, and the one or more factors include the spatial coordinates of the object.

Preferably, receiving the plurality of signals comprises receiving at least four values of a signal $M_i$ at the at least four frequencies, and determining the one or more factors includes:

determining a value of a position signal amplitude $A_0$, generated responsive to the unperturbed energy field, by substituting respective values of the signal $M_i$ into an equation $$\overline{M}_i = \overline{A}_i + a_i' e^{i\phi_i'}$$

wherein $\overline{M}_i$ is a phasor representing a measured field, $\overline{A}_i$ is a phasor representing the unperturbed field, $a_i'$ represents an amplitude of the perturbing field, $\phi_i'$ represents a phase of the perturbing field, and i represents at least four numbers respectively corresponding to the at least four frequencies, so as to generate at least four equations; and solving the at least four equations for the position signal amplitude $A_0$.

There is further provided, according to a preferred embodiment of the present invention, object tracking apparatus, comprising:

a radiator, which generates an energy field at a plurality of predetermined frequencies in the vicinity of the object;

a sensor, fixed to the object, which generates a plurality of signals responsive to the energy field and to an interfering article responsive to the energy field; and signal processing circuitry, which receives the plurality of signals from the sensor and determines an optimal frequency for the energy field from amongst the plurality of predetermined frequencies responsive to a parameter of the signals, and which determines position coordinates of the object responsive to the signal at the optimal frequency.

Preferably, the radiator generates the energy field at the plurality of predetermined frequencies by scanning the frequencies sequentially.

Further preferably, the radiator generates the energy field at the plurality of predetermined frequencies by multiplexing at least some of the frequencies.

Preferably, the parameter includes a phase shift, and the optimal frequency includes the frequency where the phase shift is a minimum.

Preferably, the signal processing circuitry determines the position coordinates of the object responsive to an amplitude of one of the plurality of signals at the frequency where the phase shift is a minimum.

Preferably, the energy field includes a magnetic field.

Preferably, the plurality of signals include a plurality of electrical signals which are generated responsive to the magnetic field.

There is further provided, according to a preferred embodiment of the present invention, object tracking apparatus, including:

a radiator, which generates an energy field including a plurality of predetermined frequencies in the vicinity of the object;

a sensor, fixed to the object, which generates a respective plurality of signals responsive to the energy field and to an interfering article responsive to the energy field; and signal processing circuitry, which receives the plurality of signals from the sensor and determines one or more factors conditional on spatial coordinates of the object responsive to the signals and their corresponding frequencies.

Preferably, the plurality of frequencies includes at least four frequencies, and wherein the one or more factors comprise the spatial coordinates of the object.

The present invention will be more fully understood from the following detailed description of the preferred embodiments thereof, taken together with the drawings, in which:

DETAILED DESCRIPTION OF PREFERRED EMBODIMENTS

Figure 2:
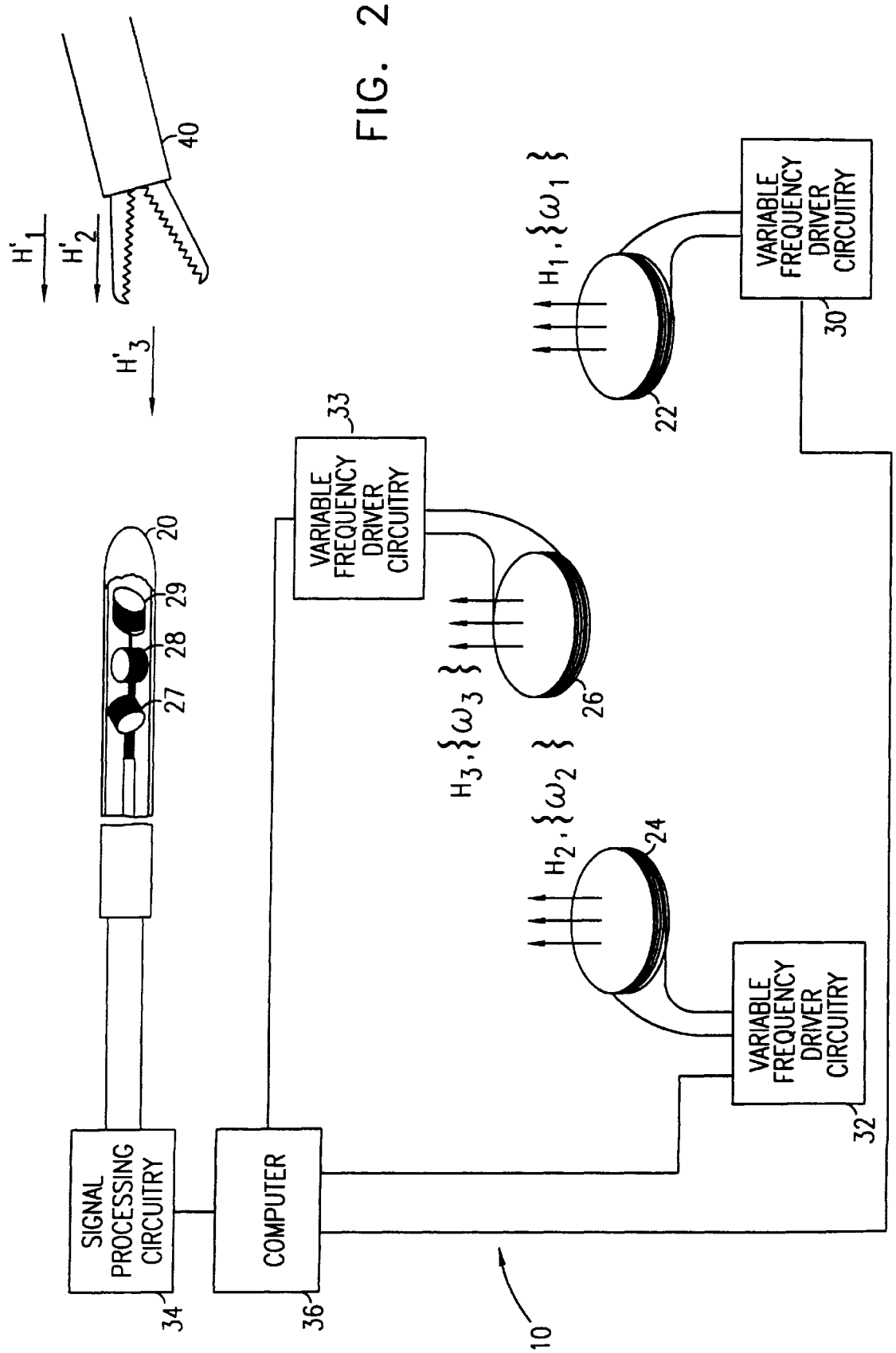
FIG. 2 schematically illustrates a system for tracking a probe, such as a catheter for medical use, according to a preferred embodiment of the present invention.

Reference is now made to FIG. 2, which schematically illustrates a system 10 for tracking a probe 20, such as a catheter for medical use, according to a preferred embodiment of the present invention. The operation of systems generally similar to system 10 are described in detail in the above-mentioned U.S. patent application Ser. No. 09/173, 763, U.S. Pat. No. 5,391,199, and PCT patent publication WO/96/05768, whose disclosures are assigned to the assignee of the present invention, and which are incorporated herein by reference. System 10 comprises a plurality of radiator coils 22, 24 and 26. These coils generate respective magnetic fields H, H and $\vec{H}_3$, at respective sets of frequencies $\{\omega_1\}$, $\{\omega_2\}$ and $\{\omega_3\}$, in the vicinity of probe 20. Each frequency set $\{\omega_1\}$, $\{\omega_2\}$ and $\{\omega_3\}$, comprises a plurality of individual frequencies. Most preferably, each of frequencies $f_i$ in sets $\{\omega_1\}$, $\{\omega_2\}$ and $\{\omega_3\}$ is simply divisible by a common frequency $f_0$, i.e., $f_i=k_1 f_0$ where $k_1$ is a whole number. In this case, a sampling period $\Delta T$ circuitry receiving radiated signals, which signals are explained in more detail hereinbelow, is preferably given by the following equation:

$$\Delta T = \frac{k_2}{f_0} \qquad (1)$$

where $k_2$ represents a whole number.

Typical values of frequencies $f_i$ in sets $\{\omega_1\}$, $\{\omega_2\}$ and $\{\omega_3\}$ comprise frequencies in the range 100 Hz–20 kHz.

System 10 further comprises substantially similar variable frequency driver circuitry 30, 32 and 33, coupled to each of the radiator coils, which drive coils 22, 24 and 26 at the respective sets of frequencies $\{\omega_1\}$, $\{\omega_2\}$ and $\{\omega_3\}$. Most preferably, the sets of frequencies $\{\omega_1\}$, $\{\omega_2\}$ and $\{\omega_3\}$ at which the coils radiate are set by computer 36. Further most preferably, at least some of the frequencies of each driver circuitry are multiplexed together, and after acquisition the resulting signals are analyzed in signal processing circuitry 34, as described in more detail below. Alternatively, the frequency of each driver circuitry is varied according to some other method known in the art, such as scanning the frequencies cyclically over time, and/or using one or more other methods of time multiplexing. Whichever method is used to vary the frequencies, at any instant in time a frequency radiated by a specific coil is set to be different from the frequency or frequencies radiated by all the other coils.

The probe includes sensor coils 27, 28 and 29, which generate electrical current signals in response to the magnetic fields. At any instant in time these signals comprise components of the specific frequencies $\{\omega_1\}$, $\{\omega_2\}$ and $\{\omega_3\}$ being generated, whose respective amplitudes are dependent on the position and orientation of probe 20. The signals generated by sensor coils 27, 28 and 29 are preferably received and processed by signal processing circuitry 34 and then used by computer 36 to calculate position and orientation coordinates of probe 20.

FIG. 2 shows three radiator coils 22, 24 and 26 and three sensor coils 27, 28 and 29 in a probe 20. It will be understood, however, that the present invention is equally applicable to tracking systems comprising one, two, four or more radiator coils and one, two or more sensor coils. For example, the present invention applies to a single axis system comprising one sensor coil, in which case the system most preferably comprises nine radiator coils.

In the absence of parasitic effects, the signals generated by sensor coils 27, 28 and 29 at any of frequencies $\{\omega_1\}$ are proportional to the amplitude of the time derivative of the projection of field $\vec{H}_1$ at probe 20 along the respective axes of the sensor coils. The signals generated at any of frequencies $\{\omega_2\}$ and $\{\omega_3\}$ are similarly proportional to the projections of $\vec{H}_2$ and $\vec{H}_3$. Parasitic effects that may arise due to mutual inductance among the radiator coils are preferably substantially eliminated, as disclosed, for example, in PCT patent application no. PCT/IL/00100, filed Mar. 18, 1997, which is assigned to the assignee of the present patent application, and whose disclosure is incorporated herein by reference.

Since the direction and amplitude of the magnetic field due to any one of radiator coils 22, 24 and 26 can be calculated easily using methods known in the art, the sensor coil signals due to the respective radiator coil field may be directly related to the sensor coil's distance from and orientation relative to the radiator coil. It will also be appreciated that in the absence of parasitic magnetic fields, such as will be described below, the phase of the signal at each specific frequency comprised in $\{\omega_1\}$, $\{\omega_2\}$ and $\{\omega_3\}$ is substantially constant relative to the phase of the magnetic field generated by radiator coils 22, 24, 26, and depends on the position and orientation of sensor coils 27, 28, 29.

As shown in FIG. 2, however, when a metal or magnetic field-responsive article, for example a surgical tool 40, is introduced into the vicinity of probe 20, the article will generally receive energy from unperturbed fields $\vec{H}_1$, $\vec{H}_2$ and $\vec{H}_3$, and re-radiate perturbing parasitic magnetic fields, $\vec{H}'_1$, $\vec{H}'_2$ and $\vec{H}'_3$, at the specific frequencies from sets $\{\omega_1\}$, $\{\omega_2\}$ and $\{\omega_3\}$ which are being generated. Generally the phases of the parasitic fields will be shifted relative to the radiator coil fields by phase angles $\phi_1'$, $\phi_2'$ and $\phi_3'$, respectively. The phases and amplitudes of the parasitic fields generally depend on properties of tool 40, including its dielectric constant, magnetic permeability, geometrical shape and orientation relative to the radiator coils. The phases and amplitudes of the parasitic fields are also a function of the specific frequencies being generated.

Figure 3:
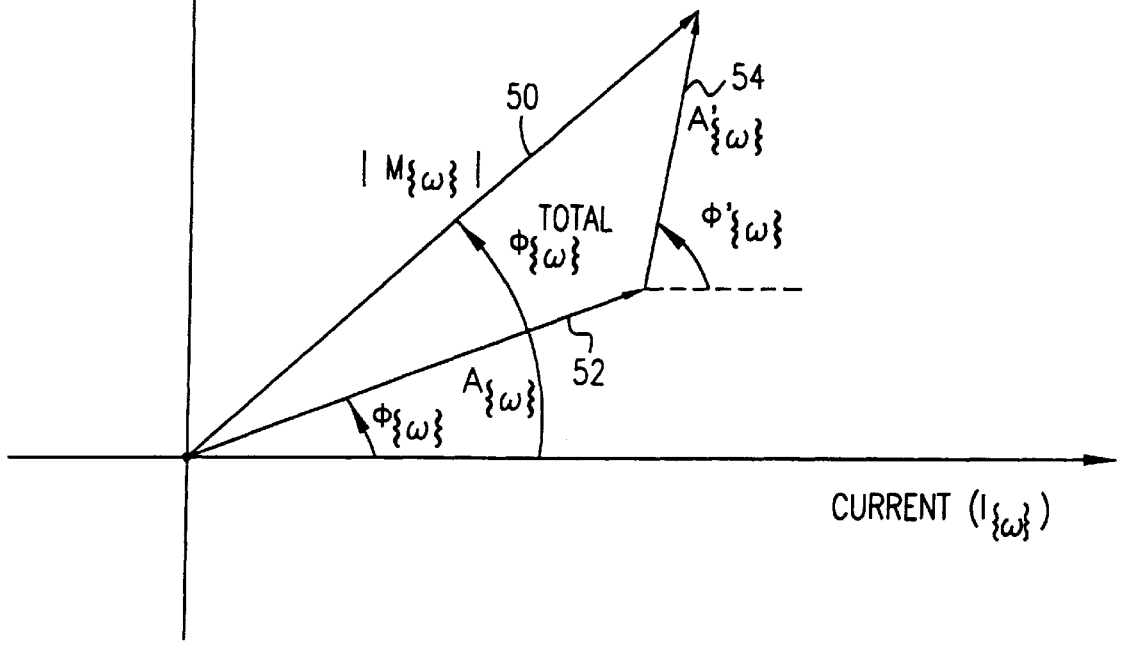
FIG. 3 is a vector diagram illustrating a relation between position and parasitic components of a signal generated in the system of FIG. 2, according to a preferred embodiment of the present invention.

FIG. 3 is a vector diagram illustrating a relation between the position and parasitic signal components, for radiation from radiator coil 22 at sensor coil 27, according to a preferred embodiment of the present invention. Coil 27 generates a set of frequencies, responsive to the frequencies generated by radiator coils 22, 24 and 26, which are transferred to signal processing circuitry 34. Circuitry 34 separates the received signal into constituent frequencies, and recovers the amplitude and phase of each frequency, which are used as described hereinbelow with reference to FIG. 3. In the interests of simplicity, unless indicated otherwise the following explanation refers to sensor coil 27, although it will be appreciated that sensor coil 28, and 29 behave substantially as coil 27.

Signal vector 50, having an amplitude $|M_{\{\omega\}}|$ and a phase $\phi_{\{\omega\}}^{total}$, represents a signal $M_{\{\omega\}}$ received from sensor coil 27 at a set of frequencies $\{\omega\}$. Vector 50 is the vector sum of position signal component vector 52 and parasitic signal component vector 54. Vectors 50, 52, and 54 are referenced in phase to a current $I_{\{\omega\}}$ in coil 27. Position signal component 52 has amplitude $A_{\{\omega\}}$ and a substantially constant baseline phase $\phi_{\{\omega\}}$ at frequency $\{\omega\}$. At frequency $\{\omega\}$ parasitic signal component 54 has a phase shift from the baseline of $\phi_{\{\omega\}}'$ and an amplitude $A_{\{\omega\}}'$. Unless indicated otherwise, the following explanation considers one specific frequency, herein termed $\omega$, although it will be appreciated that the explanation applies to all frequencies generated in coil 27.

The total combined signal $M_\omega$ received from sensor coil 27, including both position and parasitic signal components may generally be expressed as:

$$\overline{M}_\omega = \overline{A}_\omega + \overline{A}'_\omega \tag{2a}$$

so that the amplitude $|M_\omega|$ is given by $$|\overline{M}_\omega| = |\overline{A}_\omega + \overline{A}'_\omega| \tag{2b}$$

wherein $\overline{A}_\omega$ and $\overline{A}'_\omega$ are the phasors of the position signal component and the parasitic signal component respectively, at frequency $\omega$.

It will be observed in equation (2b) and from FIG. 3 that for each of the signal frequency components $|M_\omega|$, the superposition of the parasitic signal component will cause a phase shift in the total detected signal, relative to the signal phase in the absence of metal tool 40, given by:

$$\phi_\omega^{total} = \arctan\left[\frac{A_\omega \sin\phi_\omega + A'_\omega \sin\phi'_\omega}{A_\omega \cos\phi_\omega + A'_\omega \cos\phi'_\omega}\right] \tag{3}$$

In preferred embodiments of the present invention, signal processing circuitry 34 and computer 36 detect and record baseline phases $\phi_\omega$ for all different frequencies received from sensor coils 27, 28 and 29, or for other systems described hereinabove such as the single axis system, in the absence of any metal or other interfering magnetic field-responsive objects in the vicinity of probe 20. Alternatively, undisturbed phases of the position signal components may have been determined in advance for system 10 or are known based on the operation of the system. When metal tool 40 is introduced into the vicinity of probe 20, the phase shift due to the parasitic components engendered thereby in the signals is measured at each separate frequency.

Figure 4:
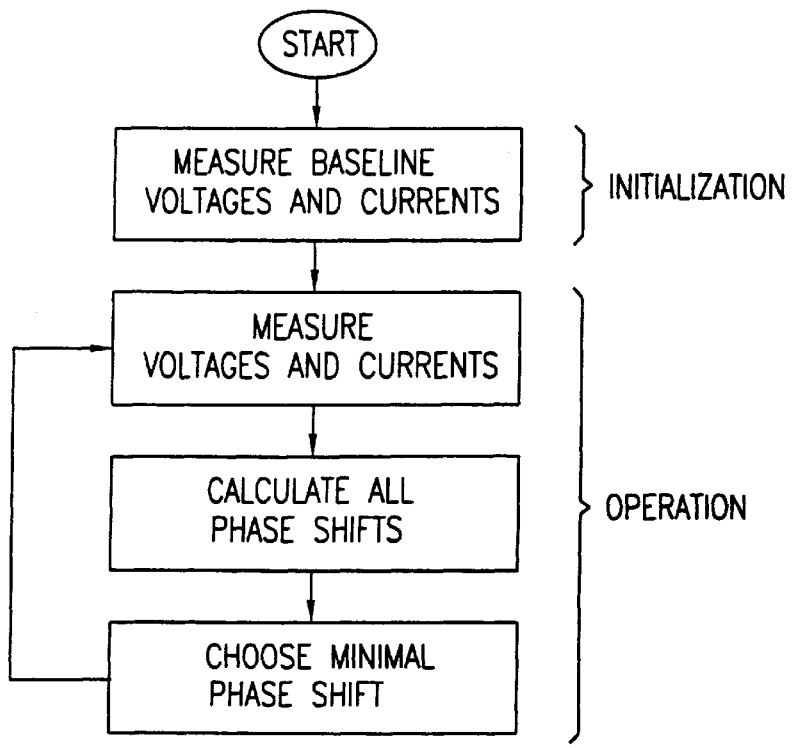
FIG. 4 is a schematic flow chart showing a method for choosing frequencies to track the probe of the system of FIG. 2, according to a preferred embodiment of the present invention.

FIG. 4 is a schematic flow chart showing a method for choosing frequencies to track probe 20, according to a preferred embodiment of the present invention. For simplicity, the following description refers only to radiator coil 22 and sensor coil 27, but it will be understood that the method shown in FIG. 4 applies to any combination of a radiator coil and a sensor coil in system 10. In an initialization phase a baseline phase value $\phi_\omega$ is measured by circuitry 34 from the voltages and currents induced in coil 27. The baseline phase value $\phi_\omega$ is measured at each of the frequencies of $\{\omega_1\}$ and each value is recorded in computer 36. During an operation phase the value of total and the absolute value of the difference, $|\phi_\omega^{total} - \phi_\omega|$, is measured and recorded for each frequency of $\{\omega_1\}$. In the event that the absolute difference is not equal to zero, indicating that a parasitic signal component due to tool 40 is present, computer 36 selects the frequency having the smallest absolute difference. This frequency is used when evaluating $|M_\omega|$ in equation (2b). It will be appreciated that applying the method described hereinabove to all combinations of radiator coils and sensor coils in system 10 enables a complete determination of the position and orientation of probe 20.

As stated hereinabove, equations (2a) and (2b) apply for frequency $\omega$ applied to sensor coil 27. As the frequency $\omega$ is varied, values of $A_\omega$, $\phi_\omega$, $A_\omega'$ and $\phi_\omega'$ vary. As is known in the art, values of $A_\omega$ and $A_\omega'$ are directly proportional to the current at which the specific radiator coil, assumed herein to be radiator coil 22, generating the field is being driven and which sensor coil 27 is detecting. Thus $A_\omega = \beta A_0$, and $A_\omega' = \beta A_0'$ where $\beta$ is a constant, $\omega_0$ is an arbitrary frequency in $\{\omega_1\}$, and $A_0$ and $A_0'$ are the amplitudes of the position and parasitic signal components at frequency $\omega_0$. Also, for small variations of frequency $\omega$, $\phi_\omega'$ is linearly dependent on frequency co, so that $$\phi_\omega' = \phi_0' + \gamma \Delta \omega \quad (4)$$

where $\Delta \omega = \omega - \omega_0$, $\gamma$ is a constant, corresponding to a value of the derivative $$\frac{\Delta \phi}{\Delta \omega},$$

$\phi_\omega'$ is the parasitic phase and
$\phi_0'$ is the position phase.

At a particular frequency $\omega_i$, equation (2a) can be rewritten as:

$$\overline{M}_i = \overline{A}_i + \overline{A}_i' \quad (5a)$$

where $\overline{M}_i$ is a phasor representing the measured field at $\omega_i$,
$\overline{A}_i$ is a phasor representing the unperturbed field, and
$\overline{A}_i'$ is a phasor representing the perturbing field due to tool 40.

Equation (5a) can be rewritten as follows:

$$\overline{M}_i = \overline{A}_i + a_i' e^{i\phi_i'} \quad (5b)$$

where $a_i'$ and $\phi_i'$ are the perturbing amplitude and phase at $\omega_i$.

Equation (5b) can also be rewritten:

$$\overline{M}_i = \beta_i |A_0| e^{i\phi_i} + \beta_i a_0' e^{i(\phi_0' + \gamma(\omega^i - \omega^0))} \quad (5c)$$

where $a_0'$ and $\phi_0'$ are the perturbing amplitude and phase, and $A_0$ is the unperturbed amplitude, at $\omega_0$,
$\phi_i$ is the unperturbed phase shift at $\omega i$, $$\beta_i = \left| \frac{\overline{M}_i}{\overline{M}_0} \right|, \text{ and } \gamma = \frac{\partial \phi}{\partial \omega}.$$

Figure 1:
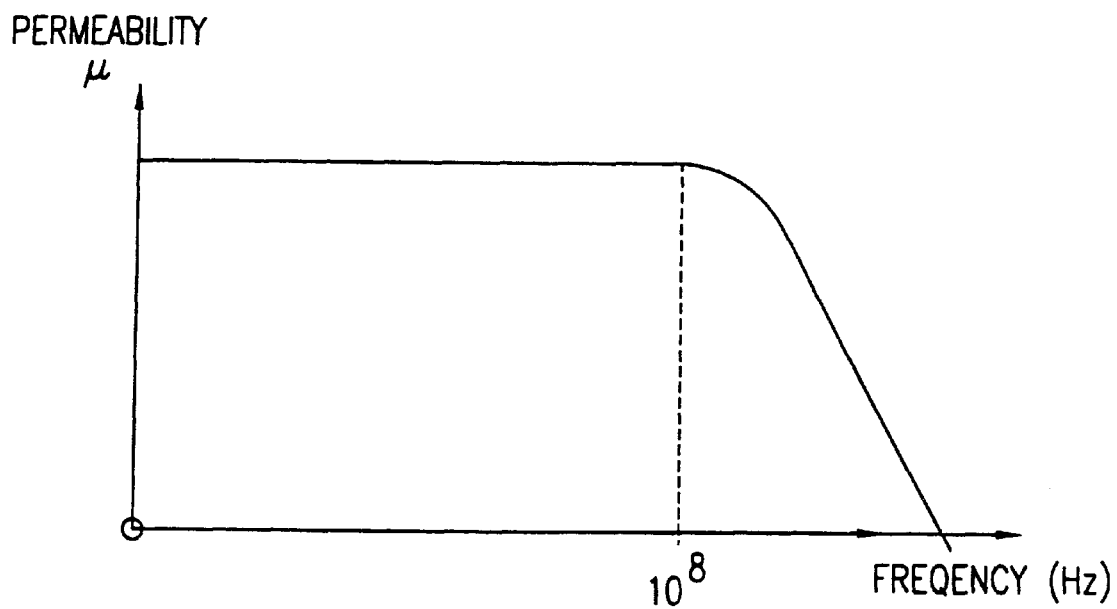
FIG. 1 is a graph showing a relation of the permeability $\mu$ of a ferromagnetic material in a magnetic field vs. frequency f at which the field is being generated, as is known in the art.

In equation (5c) $A_0$, $a_0'$, and $\phi_0'$ are unknown, and $\phi_i$, $\beta_i$, $\gamma$, $\omega_0$, and $\omega_i$ are known, or in the case of $\gamma$ may be found from one other frequency apart from $\omega_0$ and $\omega_i$ by using the graph of FIG. 1 relating permeability to frequency. Alternatively, $\gamma$ may be assumed to be unknown. Thus, if $\overline{M}_i$ is measured at four known separate frequencies, equation (5c) can be solved for $A_0$, the position signal component. Most preferably, frequencies $\{\omega_1\}$, $\{\omega_2\}$ and $\{\omega_3\}$ in system 10 comprise more than four separate frequencies, so that a plurality of values of $A_0$ can be determined, and a final value of $A_0$ calculated by one of the processes of averaging known in the art. Alternatively or additionally, when frequencies $\{\omega_1\}$, $\{\omega_2\}$ and $\{\omega_3\}$ in system 10 comprise more than four separate frequencies, equation (5c) may be adapted to comprise other parameters describing at least some $A_0$, $a_0'$, and $\phi_0'$. For example, values of $A_0$ and $a_0'$ can be assumed to depend on frequency $\omega$ in a linear or a non-linear manner, and appropriate constants can be included in equation (5c), as is known in the art.

It will thus be appreciated that by varying the excitation frequency of each radiator coil, and measuring the total signal generated in each sensor coil at these frequencies, the position component of the signal can be determined regardless of the presence of parasitic components. It will also be appreciated that varying the excitation frequency of each radiator coil by a plurality of frequencies, wherein the plurality is fewer than four, will give useful information regarding factors associated with tracking objects in the presence of interfering articles.

It will further be appreciated that the preferred embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

What is claimed:

1. A method for tracking an object, comprising:
   producing an unperturbed energy field at a plurality of predetermined frequencies in the vicinity of the object;
   measuring a baseline phase value $\phi_\omega$ of each of the plurality of resultant signals at the respective plurality of predetermined frequencies before introduction of the article;
   determining a characteristic of a perturbing energy field induced responsive to the unperturbed field, due to introduction of an article responsive to the unperturbed field into the vicinity of the object;
   receiving a plurality of resultant signals responsive to the unperturbed and perturbing energy fields generated at a location of the object after introduction of the article;
   measuring a phase shift $\phi_\omega^{total}$ at the respective plurality of predetermined frequencies after introduction of the article, so that the parameter comprises a term $|\phi_\omega^{total} - \phi_\omega|$ for each of the plurality of predetermined frequencies;
   determining an optimal frequency for the unperturbed energy field from amongst the plurality of predetermined frequencies responsive to a parameter of the resultant signals by determining a frequency $\omega$ at which $|\phi_\omega^{total} - \phi_\omega|$ a is a minimum; and
   determining spatial coordinates of the object responsive to the resultant signal at the optimal frequency.

2. A method according to claim 1, wherein producing the unperturbed energy field at the plurality of predetermined frequencies comprises scanning the frequencies sequentially.

3. A method according to claim 1, wherein producing the unperturbed energy field at the plurality of predetermined frequencies comprises multiplexing at least some of the frequencies.

4. A method according to claim 1, wherein determining spatial coordinates of the object comprises determining spatial coordinates responsive to an amplitude of a signal $|M_\omega|$ at the frequency $\omega$.

5. A method according to claim 1, wherein determining spatial coordinates of the object comprises determining spatial coordinates responsive to a phase of a signal $M_\omega$ at the frequency $\omega$.

6. A method according to claim 1, wherein producing the energy fields comprises producing magnetic fields.

7. A method according to claim 6, wherein receiving the signals comprises receiving electrical signals which are generated responsive to the magnetic fields.

8. A method for tracking an object, comprising:

producing an unperturbed energy field comprising a plurality of predetermined frequencies in the vicinity of the object;

producing a perturbing energy field by introduction of an article responsive to the unperturbed field into the vicinity of the object;

receiving a respective plurality of signals responsive to the unperturbed and perturbing energy fields generated at a location of the object after introduction of the article;

determining one or more factors conditional on spatial coordinates of the object responsive to the plurality of signals and the respective frequencies by assuming a phasor $\overline{A}_\omega$ of a signal responsive to the unperturbed energy field and a phasor $\overline{A}'_\omega$ of a signal responsive to the perturbing energy field to be directly proportional to a plurality of predetermined currents generating the fields; and assuming a phase $\phi_\omega$ of the signal responsive to the unperturbed energy field and a phase $\phi_\omega$ of the signal responsive to the perturbing energy field to be linearly dependent on the plurality of predetermined frequencies.

9. A method according to claim 8, wherein the plurality of frequencies comprises at least four frequencies, and wherein the one or more factors comprise the spatial coordinates of the object.

10. A method according to claim 9, wherein receiving the plurality of signals comprises receiving at least four values of a signal $M_i$ at the at least four frequencies, and wherein determining the one or more factors comprises:

determining a value of a position signal amplitude $A_0$, generated responsive to the unperturbed energy field, by substituting respective values of the signal $M_i$ into an equation $$\overline{M}_i = \tilde{A}_i + a_i' e^{i\phi_i'}$$

wherein $\overline{M}_i$ is a phasor representing a measured field, $\overline{A}_i$ is a phasor representing the unperturbed field, $a_i'$ represents an amplitude of the perturbing field, $\phi_i'$ represents a phase of the perturbing field, and i represents at least four numbers respectively corresponding to the at least four frequencies, so as to generate at least four equations; and solving the at least four equations for the position signal amplitude $A_0$.

11. Object tracking apparatus, comprising:

a radiator, which generates an energy field at a plurality of predetermined frequencies in the vicinity of the object;

a sensor, fixed to the object, which generates a plurality of signals responsive to the energy field and to an interfering article responsive to the energy field; and signal processing circuitry, which receives the plurality of signals from the sensor and determines an optimal frequency for the energy field from amongst the plurality of predetermined frequencies responsive to a parameter of the signals by measuring a baseline phase value $\phi_\omega$ of each of the plurality of resultant signals at the respective plurality of predetermined frequencies before introduction of the article; and measuring a phase shift $\phi_\omega^{total}$ at the respective plurality of predetermined frequencies after introduction of the article, so that the parameter comprises a term $|\phi_\omega^{total} - \phi_\omega|$ for each of the plurality of predetermined frequencies, and which determines position coordinates of the object responsive of the object responsive to the signal at the optimal frequency by determining a frequency $\omega$ at which $|\phi_\omega^{total} - \phi_\omega|$ is a minimum.

12. Apparatus according to claim 11, wherein the radiator generates the energy field at the plurality of predetermined frequencies by scanning the frequencies sequentially.

13. Apparatus according to claim 11, wherein the radiator generates the energy field at the plurality of predetermined frequencies by multiplexing at least some of the frequencies.

14. Apparatus according to claim 11, wherein the parameter comprises a phase shift, and wherein the optimal frequency comprises the frequency where the phase shift is a minimum.

15. Apparatus according to claim 14, wherein the signal processing circuitry determines the position coordinates of the object responsive to an amplitude of one of the plurality of signals at the frequency where the phase shift is a minimum.

16. Apparatus according to claim 11, wherein the energy field comprises a magnetic field.

17. Apparatus according to claim 16, wherein the plurality of signals comprise a plurality of electrical signals which are generated responsive to the magnetic field.

18. Object tracking apparatus, comprising:

a radiator, which generates an energy field comprising a plurality of predetermined frequencies in the vicinity of the object;

a sensor, fixed to the object, which generates a respective plurality of signals responsive to the energy field and to an interfering article responsive to the energy field; and signal processing circuitry, which receives the plurality of signals from the sensor and determines one or more factors conditional on spatial coordinates of the object responsive to the signals and their corresponding frequencies by assuming a phasor $\overline{A}_\omega$ of a signal responsive to the unperturbed energy field and a phasor $\overline{A}'_\omega$ of a signal responsive to the perturbing energy field to be directly proportional to a plurality of predetermined currents generating the fields; and assuming a phase $\phi_\omega$ of the signal responsive to the unperturbed energy field and a phase $\phi_\omega'$ of the signal responsive to the perturbing energy field to be linearly dependent on the plurality of predetermined frequencies.

19. Apparatus according to claim 18, wherein the plurality of frequencies comprises at least four frequencies, and wherein the one or more factors comprise the spatial coordinates of the object.

* * * * *